(12) United States Patent
Raheem et al.

(10) Patent No.: US 8,952,154 B2
(45) Date of Patent: Feb. 10, 2015

(54) PROCESS FOR THE PREPARATION OF LAPATINIB AND ITS DITOSYLATE SALT

(75) Inventors: Mohammed Abdul Raheem, Brantford (CA); Gamini Weeratunga, Ancaster (CA); Carlos Zetina-Rocha, Brantford (CA); Eduardo Gustavo Cammisa, Oshawa (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 13/997,424

(22) PCT Filed: Dec. 23, 2011

(86) PCT No.: PCT/CA2011/001420
§ 371 (c)(1),
(2), (4) Date: Sep. 26, 2013

(87) PCT Pub. No.: WO2012/083440
PCT Pub. Date: Jun. 28, 2012

(65) Prior Publication Data
US 2014/0018535 A1    Jan. 16, 2014

Related U.S. Application Data

(60) Provisional application No. 61/427,092, filed on Dec. 23, 2010.

(51) Int. Cl.
*C07D 239/72* (2006.01)
*C07D 405/04* (2006.01)
*A61K 31/517* (2006.01)

(52) U.S. Cl.
CPC ............ *C07D 405/04* (2013.01); *A61K 31/517* (2013.01)
USPC .......................................... 544/293

(58) Field of Classification Search
CPC .................................................... C07D 405/04
See application file for complete search history.

(56) References Cited

U.S. PATENT DOCUMENTS

6,713,485 B2    3/2004   Carter et al.

FOREIGN PATENT DOCUMENTS

| WO | WO 0202552 | 1/2002 |
|---|---|---|
| WO | WO 2010017387 | 2/2010 |
| WO | WO 2010017387 A2 * | 2/2010 |
| WO | WO 2010061400 | 6/2010 |
| WO | WO2010061400 A1 * | 6/2010 |
| WO | WO 2011116634 | 9/2011 |
| WO | WO 2011160594 | 12/2011 |

OTHER PUBLICATIONS

Station. "Reductive Amination Review." (C) May 2005. Available from: < http://www.erowid.org/archive/rhodium/chemistry/reductive.amination.htm >.*
Myers. (c) Jun. 28, 2010. "Reduction." Available from: < http://web.archive.org/web/20100628101804/http://www.chem.harvard.edu/groups/myers/handouts/1_Reduction.pdf >.*
Jhung, S.H., et al. "Effect of Preparation Conditions on the Hydrogenation Activity and Metal Dispersion of Pt/C and Pd/C Catalysts." Bull. Korean Chem. Soc. (2005), vol. 26, No. 4, pp. 563-568.*

* cited by examiner

*Primary Examiner* — Noble Jarrell
*Assistant Examiner* — John S Kenyon

(57) ABSTRACT

There is provided processes for preparing Lapatinib and pharmaceutically acceptable salts thereof by the reductive amination of the aldehyde of Formula II by treatment with 2-methanesulphonylethylamine followed by catalytic hydrogenation in the presence of a suitable hydrogenation catalyst.

19 Claims, No Drawings

PROCESS FOR THE PREPARATION OF LAPATINIB AND ITS DITOSYLATE SALT

TECHNICAL FIELD

This invention relates to a process for the preparation of Lapatinib (I) and its ditosylate salt thereof.

BACKGROUND

Lapatinib is a member of the 4-anilinoquinazoline class of kinase inhibitors. It is marketed in the USA as TYKERB® (Lapatinib) and is indicated in combination with: Capecitabine for the treatment of patients with advanced or metastatic breast cancer whose tumors overexpress HER2 and who have received prior therapy including an anthracycline, a taxane, and Trastuzumab and Letrozole for the treatment of postmenopausal women with hormone receptor positive metastatic breast cancer that overexpresses the HER2 receptor for whom hormonal therapy is indicated. Lapatinib inhibits ErbB-driven tumor cell growth in vitro and in various animal models. Lapatinib is present as the monohydrate of the ditosylate salt, with the chemical name N-[3-chloro-4-[(3-fluorophenyl)methoxy]phenyl]-6-[5[[[2-(methylsulfonyl)ethyl]amino]methyl]-2-furanyl]-4-quinazolinaminebis(4-methylbenzenesulfonate)monohydrate.

U.S. Pat. No. 6,713,485 relates to substituted heteroaromatic compounds, methods for their preparation, pharmaceutical compositions containing them and their use in medicine. Specifically, the invention relates to quinazoline derivatives useful in treating disorders mediated by protein tyrosine kinase activity, in particular erbB-2 and/or EGFR activity WO 2002/02552 discloses ditosylate salts of 4-quinazolineamines as well as methods of using the same in the treatment of disorders characterized by aberrant erbB family PTK activity.

WO 2010/017387 provides Lapatinib intermediates and improved processes for preparing Lapatinib intermediates. The invention also provides processes for preparing Lapatinib and Lapatinib ditosylate.

WO 2010/061400 relates to an improved and novel process for the preparation of high purity crystalline base of Lapatinib and its pharmaceutically acceptable salts. The invention further relates to intermediates according to formula (8) and formula (9) used in this process.

SUMMARY

The present invention is directed to a process for the preparation of Lapatinib and its pharmaceutically acceptable salts.

Illustrative embodiments of the present invention provide a process for the preparation of Lapatinib or a ditosylate salt thereof comprising: i) treating of a compound of Formula II:

II

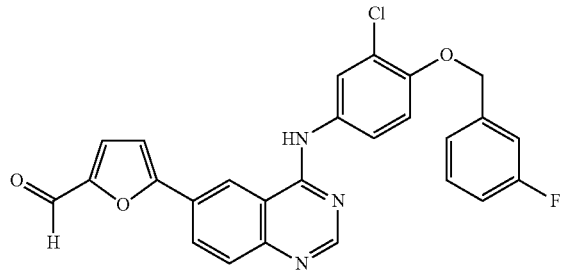

with 2-methanesulphonylethylamine or a salt thereof, thereby forming a product; and ii) reducing the product in the presence of a suitable hydrogenation catalyst, thereby forming Lapatinib free base of Formula IV:

IV

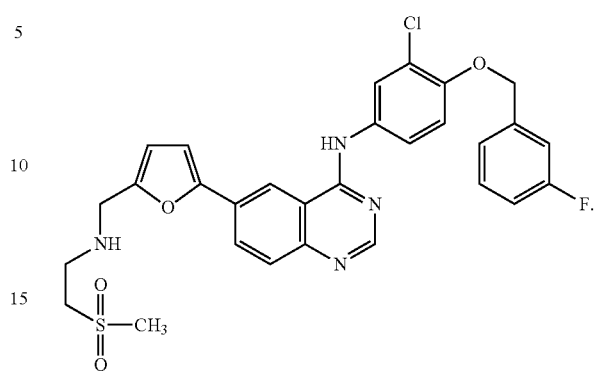

Illustrative embodiments of the present invention provide a process described herein further comprising converting the compound of Formula IV to Lapatinib ditosylate of Formula I:

I

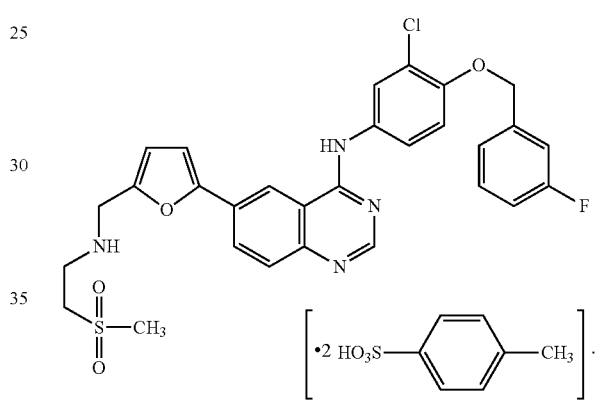

Illustrative embodiments of the present invention provide a process described herein wherein the compound of Formula IV is not isolated before converting the compound of Formula IV to the Lapatinib ditosylate of Formula I.

Illustrative embodiments of the present invention provide a process described herein wherein the converting of the compound of Formula IV to the Lapatinib ditosylate of Formula I comprises: i) treating the compound of Formula IV with about 0.8 to about 1.2 equivalents of p-toluenesulfonic acid (PTSA), thereby forming monotosylate of Formula V:

V

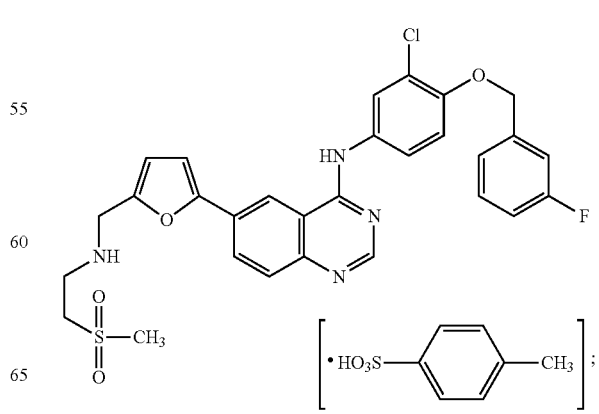

and ii) treating the compound of Formula V with about 0.8 to about 1.2 equivalents of p-toluenesulfonic acid, thereby forming the Lapatinib ditosylate of Formula I.

Illustrative embodiments of the present invention provide a process described herein wherein the conversion of a compound of Formula IV to Lapatinib ditosylate of Formula I comprises treatment of a compound of Formula IV with about 1.8 to about 2.2 equivalents of p-toluenesulfonic acid.

Illustrative embodiments of the present invention provide a process described herein whereby the process for preparation of Lapatinib ditosylate is a one-pot process in which no intermediates are isolated.

Illustrative embodiments of the present invention provide a process described herein wherein the treating of the compound of Formula II with 2-methanesulphonylethylamine or a salt thereof occurs in the presence of a first base.

Illustrative embodiments of the present invention provide a process described herein wherein the first base is N,N-diisopropylethylamine.

Illustrative embodiments of the present invention provide a process described herein wherein the hydrogenation catalyst is selected from the group consisting of palladium on carbon, platinum on carbon and Raney nickel.

Illustrative embodiments of the present invention provide a process described herein wherein the hydrogenation catalyst is palladium on carbon.

Illustrative embodiments of the present invention provide a process described herein wherein the hydrogenation catalyst is 5% palladium on carbon.

Illustrative embodiments of the present invention provide a process described herein wherein the treating of the compound of Formula II with 2-methanesulphonylethylamine or a salt thereof occurs in the presence of a first solvent selected from the group consisting of alcohols and halogenated hydrocarbons.

Illustrative embodiments of the present invention provide a process described herein wherein the treating of the compound of Formula II with 2-methanesulphonylethylamine or a salt thereof occurs in the presence of a first solvent selected from the group consisting of methanol, dichloromethane and mixtures thereof.

Illustrative embodiments of the present invention provide a composition comprising i) at least one of Lapatinib and Lapatinib ditosylate and ii) at least one of palladium, platinum and Raney nickel.

Other aspects and features of the present invention will become apparent to those ordinarily skilled in the art upon review of the following description of specific embodiments of the invention.

DETAILED DESCRIPTION

According to illustrative embodiments of the present invention, Lapatinib may be prepared according to Scheme 1 starting from compound of Formula II.

SCHEME 1

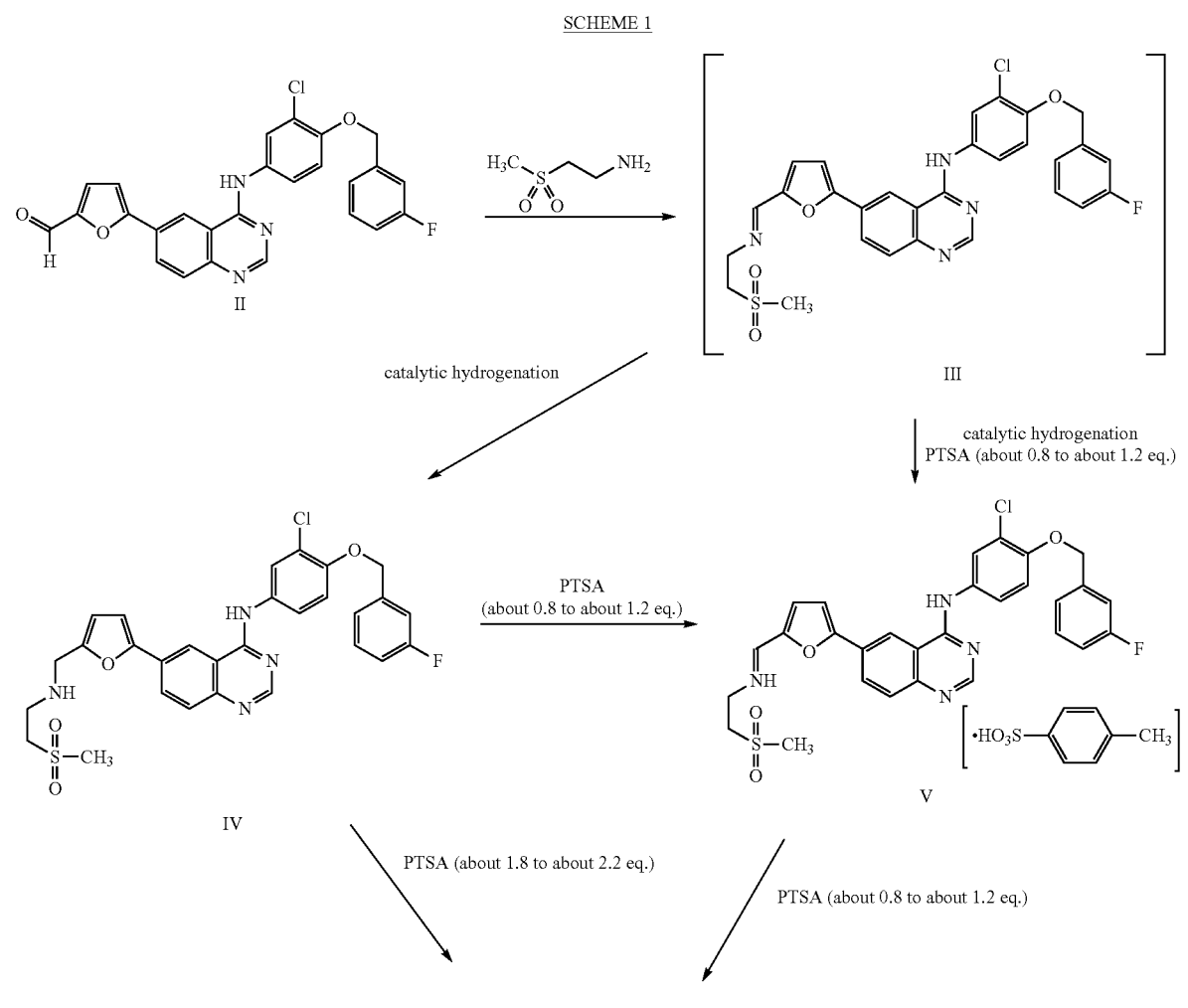

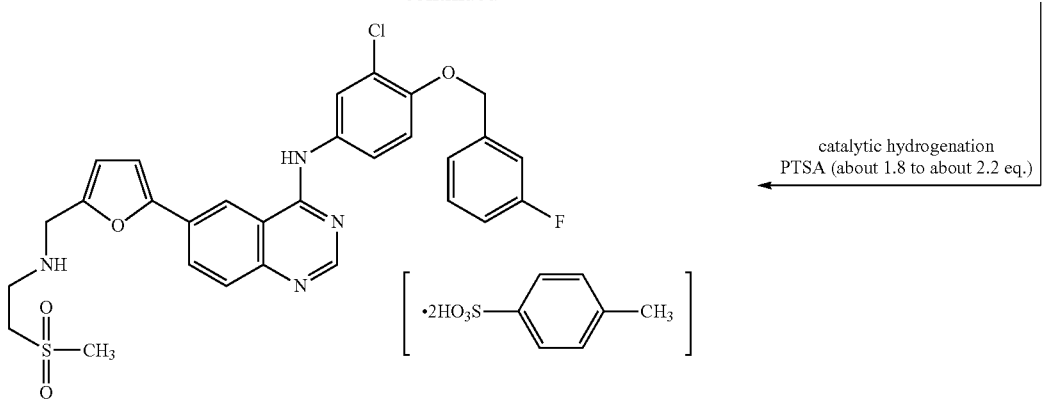

In illustrative embodiments of the present invention, there is provided a process for the preparation of Lapatinib and its ditosylate salt thereof comprising:

i. reductive amination of a compound of Formula II:

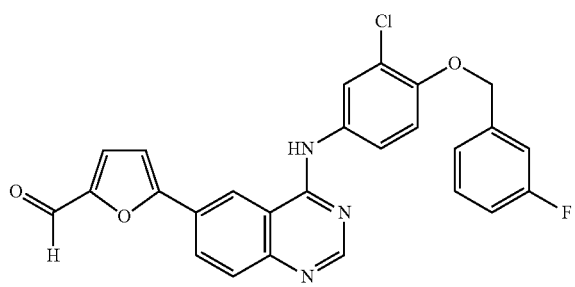

by treatment, optionally in the presence of a first base, with 2-methanesulphonylethylamine or its salt, followed by reduction by catalytic hydrogenation in the presence of a suitable hydrogenation catalyst, thereby forming Lapatinib free base of Formula IV:

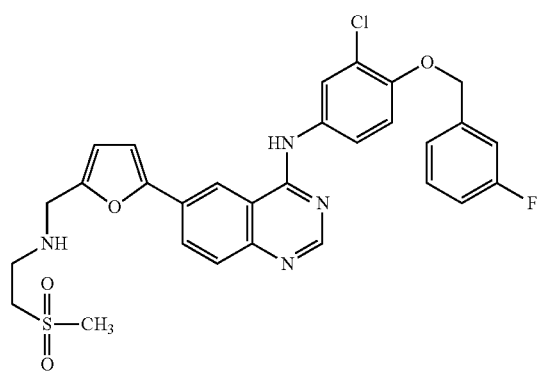

ii. optionally, conversion of the compound of Formula IV to Lapatinib ditosylate of Formula I:

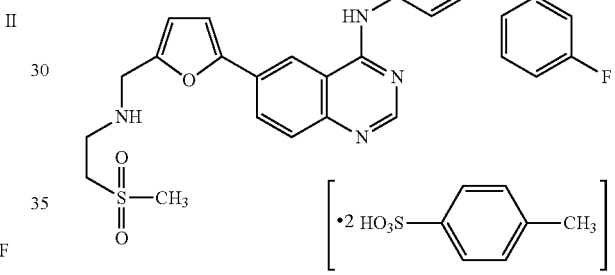

The first base may be used to liberate the free amine in a case where an acid salt of 2-methanesulphonylethylamine is used. The first base may be any suitable base capable of liberating the free amine. The first base may be inorganic or organic. The first base may be selected from the group consisting of metal hydroxides, carbonates, phosphates, tertiary amines, and aryl amines. The first base may be selected from the group consisting of sodium hydroxide, potassium hydroxide, lithium hydroxide, sodium carbonate, sodium bicarbonate, potassium carbonate, lithium carbonate, potassium phosphate, sodium phosphate, triethylamine, diisopropylamine, N,N-diisopropylethylamine, N,N-dimethylaniline, N,N-diethylaniline, pyridine and mixtures thereof.

The reductive amination may be conducted in a first solvent. The first solvent may be a suitable protic or aprotic organic solvent. The first solvent may be selected from the group consisting of alcohols (e.g. methanol, ethanol, propanol, isopropanol, butanol), alkyl ethers (e.g. tetrahydrofuran, dioxane, diethyl ether, methyl t-butyl ether, diisopropyl ether, butyl ether), alkyl esters (e.g. ethyl acetate, isopropyl acetate), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), halogenated hydrocarbons (e.g. dichloromethane and dichloroethane), and mixtures thereof.

The suitable hydrogenation catalyst may be selected from the group consisting of palladium, platinum, rhodium, ruthenium and nickel. Often, the hydrogenation catalyst is palladium on carbon, platinum on carbon or Raney-nickel. The catalyst loading may be from about 0.1 wt % to about 100 wt % palladium with respect to the weight of a compound of Formula II. The catalyst loading may be from about 0.1% to about 20% with respect to the weight of a compound of Formula II. The suitable hydrogenation catalyst may be finely dispersed solids or adsorbed on an inert support such as carbon or alumina. The suitable hydrogenation catalyst may be 5 wt % palladium on carbon. The hydrogenation may be performed by using hydrogen gas or transfer hydrogenation. It should also be noted that catalyst moistened with water, for instance 50% water wet 5% palladium on carbon, is also suitable.

Optionally, following the reaction of a compound of the Formula II with 2-methanesulphonylethylamine or its salt, an intermediate imine of the Formula III may be isolated prior to catalytic hydrogenation.

The reductive amination of the present invention may cleanly convert the compound of the Formula II to the compound of Formula IV in high yield with few impurities. The reaction occurs under mild conditions and does not require aqueous work-up. This clean conversion allows for preparation of ditosylate of Formula I in high yield and high purity.

The free base of Formula IV may or may not be isolated before conversion to the ditosylate of Formula I. The ditosylate of Formula I may be prepared directly from the free base of Formula IV by treatment with a sufficient quantity of p-toluenesulfonic acid. For example, treatment of the free base of Formula IV with about 1.8 to about 2.2 equivalents of p-toluenesulfonic acid yields the compound of Formula I. Alternatively, the ditosylate may be prepared stepwise, whereby the monotosylate is isolated first, followed by treatment with a second quantity of p-toluenesulfonic acid to yield the ditosylate. For example, treatment of the free base of Formula IV with about 0.8 to about 1.2 equivalents of p-toluenesulfonic acid yields the intermediate monotosylate of Formula V. Treatment of the isolated monotosylate of Formula V with a further about 0.8 to about 1.2 equivalents of p-toluenesulfonic acid yields the ditosylate of Formula I.

In an embodiment, preparation of the compound of Formula I is a one-pot process whereby reductive amination of the compound of Formula II yields a compound of Formula IV, which is treated, without isolation, with p-toluenesulfonic acid to generate the distosylate of Formula I. Conversion of the compound of Formula IV to the compound of Formula I maybe conducted in a second solvent. The second solvent may be a suitable protic or aprotic organic solvent. The second solvent may be selected from the group consisting of alcohols (e.g. methanol, ethanol, propanol, isopropanol, butanol), alkyl ethers (e.g. tetrahydrofuran, dioxane, diethyl ether, methyl t-butyl ether, diisopropyl ether, butyl ether), alkyl ester (e.g. ethyl acetate, isopropyl acetate), ketones (e.g. acetone, methyl ethyl ketone, methyl isobutyl ketone), aromatic and aliphatic hydrocarbons (e.g. toluene, xylenes, hexanes, and heptanes), nitriles (e.g. acetonitrile, propionitrile, butyronitrile, and benzonitrile), N,N-dialkylamides (e.g. N,N-dimethylformamide, N,N-dimethylacetamide, and N-methyl-2-pyrrolidinone), sulfoxides and sulfones (e.g. dimethyl sulfoxide and sulfolane), halogenated hydrocarbons (e.g. dichloromethane and dichloroethane), and mixtures thereof. Similar solvents may be employed in each step when the conversion of the compound of Formula IV to the compound of Formula I proceeds stepwise through isolated Lapatinib monotosylate (Formula V).

EXAMPLES

The following examples are illustrative of some of the embodiments of the invention described herein. These examples should not be considered to limit the spirit or scope of the invention in any way.

Example 1

Preparation of N-(3-chloro-4-{[(3-fluorophenyl)methyl]oxy}phenyl)-6-[5-({[2-(methylsulfonyl)ethyl]amino}methyl)-2-furanyl]-4-quinazolinamine, 4-methylbenzenesulfonate The suspension of 5-[4-((3-chloro-4-((3-fluorobenzyl)oxy)phenyl)amino)-quinazolin-6-yl]-2-furaldehyde (5 g, 10.6 mmoL) and 2-aminoethylmethylsulfone hydrochloride (3 g, 19 mmoL) in methanol (10 mL) and dichloromethane (25 mL) was charged with N,N-diisopropylethylamine (1.6 g, 12.7 mmoL) slowly under constant stirring at room temperature. The reaction mixture was stirred for 2-4 hours until reaction completion. The reaction mixture was charged with 5% Pd—C (750 mg) and stirred under hydrogen atmosphere (after evacuation) for 16-24 hours until reaction completion. The reaction mixture was further charged with methanol (25 mL) and dichloromethane (25 mL) and stirred for 12-16 hours. The obtained mixture was filtered, washed with 1:1 mixture of methanol (20 mL) and dichloromethane (20 mL). The yellow filtrate thus obtained was charged slowly with a solution of p-toluenesulfonic acid monohydrate (2 g, 10.6 mmoL) in methanol (5 mL). The yellow solid which precipitated out was filtered and washed with 1:1 mixture of methanol (20 mL) and dichloromethane (20 mL). The solid obtained was dried under vacuum at 40-45° C. to provide the monotosylate salt of Lapatinib (4.8 g, Yield=60%, HPLC purity>99%).

$^1$HNMR (400 MHz, DMSO-d$_6$) δ 2.28 (s, 3H), 3.14 (s, 3H), 3.49-3.44 (m, 2H), 3.58-3.61 (m, 2H), 4.42 (s, 2H), 5.28 (s, 2H), 6.85 (d, J=3.4 Hz), 1H), 7.11 (d, J=7.9 Hz, 2H), 7.15-7.20 (m, 2H), 7.25-7.35 (m, 3H), 7.42-7.52 (m, 3H), 7.73 (dd, J=8.9 & 2.1 Hz, 1H), 7.87 (d, J=8.7 Hz, 1H), 8.00 (d, J=2.1 Hz, 1H), 8.24 (dd, J=8.5 Hz, & 1 Hz, 1H), 8.61 (s, 1H), 8.87 (s, 1H), 9.17 (br s, 1H), 10.0 (s, 1H).

Example 2

Preparation of N-(3-chloro-4-{[(3-fluorophenyl)methyl]oxy}phenyl)-6-[5-({[2-(methylsulfonyl)ethyl]amino}methyl)-2-furanyl]-4-quinazolinamine, 4-methylbenzenesulfonate The suspension of 5-[4-((3-chloro-4-((3-fluorobenzyl)oxy)phenyl)amino)quinazolin-6-yl]-2-furaldehyde (5 g, 10.6 mmoL) and 2-aminoethylmethylsulfone hydrochloride (3 g, 19 mmoL) in methanol (10 mL) and dichloromethane (25 mL) was charged with N,N-diisopropylethylamine (1.6 g, 12.7 mmoL) slowly under constant stirring at room temperature. The reaction mixture was stirred for 2-4 hours until reaction completion. The reaction mixture was charged with 10% Pt—C (500 mg) and stirred under hydrogen atmosphere (after evacuation) for 16-24 hours until reaction completion. The reaction mixture was further charged with methanol (25 mL) and dichloromethane (25 mL) and stirred for 12-16 hours. The obtained mixture was filtered, washed with 1:1 mixture of methanol (20 mL) and dichloromethane (20 mL). The yellow filtrate thus obtained was slowly charged with a solution of p-toluenesulfonic acid monohydrate (2 g, 10.6 mmoL) in methanol (5 mL). The yellow solid which precipitated out was filtered and washed with 1:1 mixture of methanol (20 mL) and dichloromethane (20 mL). The solid obtained was dried under vacuum at 40-45° C. to afford the monotosylate salt of Lapatinib (5 g, Yield=61%, HPLC purity>99%).

Example 3

Preparation of N-(3-chloro-4-{[(3-fluorophenyl) methyl]oxy}phenyl)-6-[5-({[2-(methylsulfonyl) ethyl]amino}methyl)-2-furanyl]-4-quinazolinamine 4-methylbenzenesulfonate The suspension of 5-[4-((3-chloro-4-((3-fluorobenzyl) oxy)phenyl)amino)quinazolin-6-yl]-2-furaldehyde (5 g, 10.6 mmoL) in methanol (25 mL) and dichloromethane (25 mL) was charged with 2-aminoethylmethylsulfone (1.4 g, 11.2 mmoL) slowly under constant stirring at room temperature. The reaction mixture was stirred for 2-4 hours until reaction completion and then the reaction mixture was charged with 5% Pd—C (500 mg) and stirred under hydrogen atmosphere (after evacuation) for 16-24 hours until reaction completion. The reaction mixture was further charged with methanol (25 mL) and dichloromethane (25 mL) and stirred for 12-16 hours. The obtained mixture was filtered, washed with 1:1 mixture of methanol (20 mL) and dichloromethane (20 mL). The yellow filtrate thus obtained was slowly charged with a solution of p-toluenesulfonic acid monohydrate (2.2 g, 11.2 mmoL) in methanol (5 mL). The yellow solid which precipitated out was filtered and washed with 1:1 mixture of methanol (20 mL) and dichloromethane (20 mL). The solid obtained was dried under vacuum at 40-45° C. to provide the monotosylate salt of Lapatinib (6.5 g, Yield=81%, HPLC purity>99%).

$^1$HNMR (300 MHz, CDCl$_3$) δ 2.69 (dd, J=5.0, 2.2 Hz, 1H), 2.82 (t, J=4.3 Hz, 1H), 3.20-3.27 (m, 2H), 3.51-3.58 (m, 1H), 3.67-3.71 (m, 2H), 3.96-4.02 (m, 3H), 4.32 (s, 2H), 6.66 (d, J=8.7 Hz, 2H), 7.11 (d, J=8.7 Hz, 2H).

Example 4

Preparation of N-(3-chloro-4-{[(3-fluorophenyl) methyl]oxy}phenyl)-6-[5-({[2-(methylsulfonyl) ethyl]amino}methyl)-2-furanyl]-4-quinazolinamine 4-methylbenzenesulfonate The suspension of 5-[4-((3-chloro-4-((3-fluorobenzyl) oxy)phenyl)amino)-quinazolin-6-yl]-2-furaldehyde (20 g, 42.2 mmoL) in methanol (100 mL) and dichloromethane (60 mL) was charged with 2-aminoethylmethylsulfone (5.8 g, 46.4 mmoL) slowly under constant stirring at room temperature and then the reaction mixture was stirred for 2-4 hours until reaction completion. The reaction mixture was charged with 5% Pd—C (1 g) and stirred under hydrogen atmosphere (after evacuation) for 16-24 hours until reaction completion. The obtained mixture was filtered, washed with 3:1 mixture of methanol (40 mL) and dichloromethane (20 mL). The filtrate was distilled to low volume whereupon the obtained solution was slowly charged with a solution of p-toluenesulfonic acid monohydrate (8.8 g, 46.4 mmoL) in methanol (20 mL). The yellow solid which precipitated out was filtered and washed with 1:3 mixture of methanol (10 mL) and dichloromethane (30 mL). The solid obtained was dried under vacuum at 40-45° C. to furnish the monotosylate salt of Lapatinib (23.7 g, Yield=75%, HPLC purity>99%).

$^1$HNMR (300 MHz, CDCl$_3$) δ 2.69 (dd, J=5.0, 2.2 Hz, 1H), 2.82 (t, J=4.3 Hz, 1H), 3.20-3.27 (m, 2H), 3.51-3.58 (m, 1H), 3.67-3.71 (m, 2H), 3.96-4.02 (m, 3H), 4.32 (s, 2H), 6.66 (d, J=8.7 Hz, 2H), 7.11 (d, J=8.7 Hz, 2H).

Example 5

Preparation of N-(3-chloro-4-{[(3-fluorophenyl) methyl]oxy}phenyl)-6-[5-({[2-(methylsulfonyl) ethyl]amino}methyl)-2-furanyl]-4-quinazolinamine 4-methylbenzenesulfonate The suspension of 5-[4-((3-chloro-4-((3-fluorobenzyl) oxy)phenyl)amino)-quinazolin-6-yl]-2-furaldehyde (10 g, 21.1 mmoL) in dichloromethane (100 mL) was charged with a solution of 2-aminoethylmethylsulfone (5.8 g, 46.4 mmoL) in methanol (50 mL) slowly under constant stirring at room temperature. The reaction mixture was stirred for 2-4 hours until reaction completion and then was charged with 5% Pd—C (0.5 g) and stirred under hydrogen atmosphere at 25 psi pressure for 16-24 hours until reaction completion. The obtained mixture was filtered, washed with a 3:1 mixture of methanol (40 mL) and dichloromethane (20 mL). The filtrate was distilled to low volume, and the obtained solution was slowly charged with solution of p-toluenesulfonic acid monohydrate (4.4 g, 23.2 mmoL) in methanol (10 mL). The yellow solid which precipitated out was filtered and washed with a 1:1 mixture of methanol (20 mL) and dichloromethane (20 mL). The solid obtained was dried under vacuum at 40-45° C. to give the monotosylate salt of Lapatinib (11.4 g, Yield=72%, HPLC purity>99%).

$^1$HNMR (300 MHz, CDCl$_3$) δ 2.69 (dd, J=5.0, 2.2 Hz, 1H), 2.82 (t, J=4.3 Hz, 1H), 3.20-3.27 (m, 2H), 3.51-3.58 (m, 1H), 3.67-3.71 (m, 2H), 3.96-4.02 (m, 3H), 4.32 (s, 2H), 6.66 (d, J=8.7 Hz, 2H), 7.11 (d, J=8.7 Hz, 2H).

Example 6

Preparation of N-(3-chloro-4-{[(3-fluorophenyl) methyl]oxy}phenyl)-6-[5-({[2-(methylsulfonyl) ethyl]amino}methyl)-2-furanyl]-4-quinazolinamine 4-methylbenzenesulfonate The suspension of 5-[4-((3-chloro-4-((3-fluorobenzyl) oxy)phenyl)amino)quinazolin-6-yl]-2-furaldehyde (10 g, 21.1 mmoL) in dichloromethane (100 mL) was charged with a solution of 2-aminoethylmethylsulfone (5.8 g, 46.4 mmoL) in methanol (50 mL) slowly under constant stirring at room temperature. The reaction mixture was stirred for 2-4 hours until reaction completion. The reaction mixture was charged with 5% Pd—C (1.5 g) and stirred under hydrogen atmosphere using balloon pressure for 12-16 hours until reaction completion. The obtained mixture was filtered through Celite® pad and rinsed with methanol (30 mL) and dichloromethane (10 mL) mixture. The filtrate was distilled to a low volume and the solution was charged with toluene (50 mL) followed by addition of the solution of p-toluenesulfonic acid monohydrate (4.8 g, 25.3 mmoL) in methanol (25 mL). The yellow solid precipitated out was filtered after 2-8 hours and washed with 1:1 mixture of methanol and toluene (40 mL). The solid obtained was dried under vacuum at 40-45° C. to provide the monotosylate salt of Lapatinib (11.4 g, Yield=93%, HPLC purity>99%).

$^1$HNMR (300 MHz, CDCl$_3$) δ 2.69 (dd, J=5.0, 2.2 Hz, 1H), 2.82 (t, J=4.3 Hz, 1H), 3.20-3.27 (m, 2H), 3.51-3.58 (m, 1H), 3.67-3.71 (m, 2H), 3.96-4.02 (m, 3H), 4.32 (s, 2H), 6.66 (d, J=8.7 Hz, 2H), 7.11 (d, J=8.7 Hz, 2H).

Example 7

Preparation of N-(3-chloro-4-{[(3-fluorophenyl)methyl]oxy}phenyl)-6-[5-({[2-(methylsulfonyl)ethyl]amino}methyl)-2-furanyl]-4-quinazolinamine bis 4-methylbenzenesulfonate The suspension of 5-[4-((3-chloro-4-((3-fluorobenzyl)oxy)phenyl)amino)quinazolin-6-yl]-2-furaldehyde (5 g, 10.6 mmoL) in dichloromethane (50 mL) was charged with a solution of 2-aminoethylmethylsulfone (3.2 g, 11.7 mmoL) in methanol (25 mL) slowly under constant stirring at room temperature. The reaction mixture was stirred for 2-4 hours until reaction completion. The reaction mixture was charged with 5% Pd—C (750 mg) and stirred under hydrogen atmosphere using balloon pressure for 12-16 hours until reaction completion. The obtained mixture was filtered through Celite® pad and rinsed with methanol (5 mL) and dichloromethane (15 mL) mixture. The filtrate was distilled to low volume and the solution was charged with dichloromethane (25 mL) followed by addition of the solution of p-toluenesulfonic acid monohydrate (4.4 g, 23.3 mmoL) in methanol (10 mL). The yellow solid which precipitated out was filtered after 2-8 hours and washed with 1:1 mixture of methanol and dichloromethane (20 mL). The solid obtained was dried under vacuum at 40-45° C. to provide Lapatinib (11.4 g, Yield=93%, HPLC purity>99%).

Example 8

Preparation of N-(3-chloro-4-{[(3-fluorophenyl)methyl]oxy}phenyl)-6-[5-({[2-(methylsulfonyl)ethyl]amino}methyl)-2-furanyl]-4-quinazolinamine The suspension of 5-[4-((3-chloro-4-((3-fluorobenzyl)oxy)phenyl)amino)quinazolin-6-yl]-2-furaldehyde (5 g, 10.6 mmoL) in dichloromethane (50 mL) was charged with a solution of 2-aminoethylmethylsulfone (3.2 g, 11.7 mmoL) in methanol (25 mL) slowly under constant stirring at room temperature. The reaction mixture was stirred for 2-4 hours until reaction completion and then was charged with 5% Pd—C (750 mg) and stirred under a hydrogen atmosphere using balloon pressure for 12-16 hours until reaction completion. The obtained mixture was filtered through Celite® pad and rinsed with methanol (5 mL) and dichloromethane (15 mL) mixture. The filtrate was distilled to low volume and the obtained solution was charged with methanol (25 mL). The reaction mixture was stirred for 2-6 hours and the yellow solid which precipitated out was filtered and washed with methanol (10 mL). The solid obtained was dried under vacuum at 40-45° C. to furnish Lapatinib freebase (5 g, Yield=85%, HPLC purity>99%).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples.

What is claimed is:

1. A process for the preparation of Lapatinib or a ditosylate salt thereof comprising:

i) treating of a compound of Formula II:

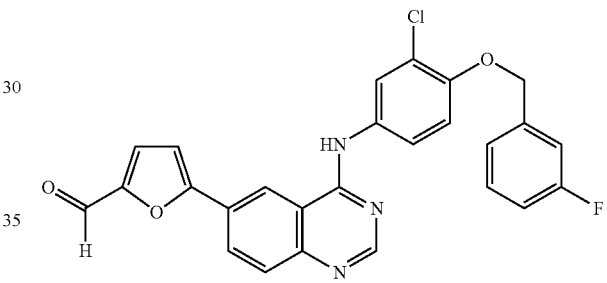

with 2-methanesulphonylethylamine or a salt thereof, thereby forming a product; and ii) reducing the product in the presence of a suitable hydrogenation catalyst, thereby forming Lapatinib free base of Formula IV:

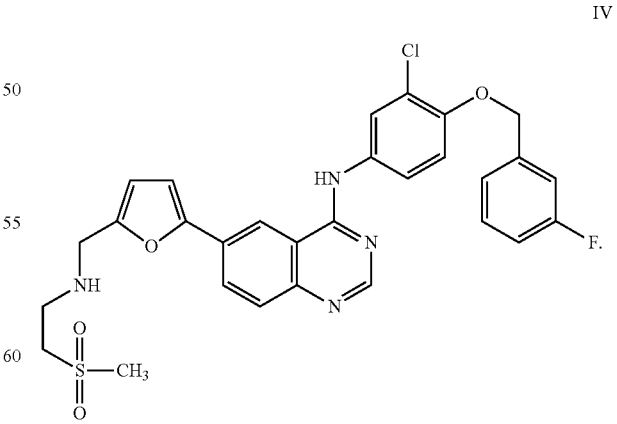

2. The process of claim 1 further comprising converting the compound of Formula IV to Lapatinib ditosylate of Formula I:

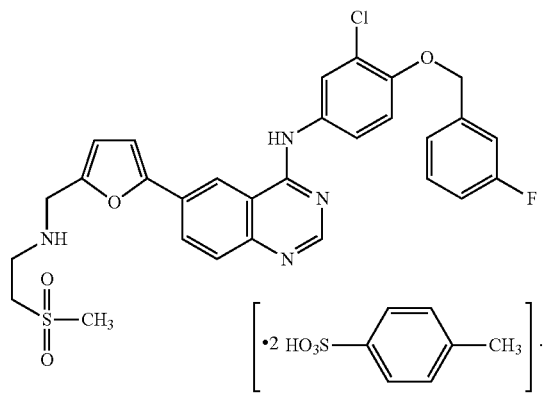

3. The process of claim 2 wherein the compound of Formula IV is not isolated before converting the compound of Formula IV to the Lapatinib ditosylate of Formula I.

4. The process of claim 2 wherein the converting of the compound of Formula IV to the Lapatinib ditosylate of Formula I comprises:
 i) treating the compound of Formula IV with about 0.8 to about 1.2 equivalents of p-toluenesulfonic acid, thereby forming monotosylate of Formula V:

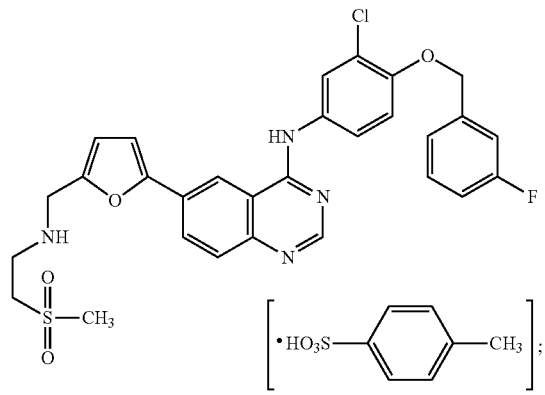

and
 ii) treating the compound of Formula V with about 0.8 to about 1.2 equivalents of p-toluenesulfonic acid, thereby forming the Lapatinib ditosylate of Formula I.

5. The process of claim 2 wherein the conversion of a compound of Formula IV to Lapatinib ditosylate of Formula I comprises treatment of a compound of Formula IV with about 1.8 to about 2.2 equivalents of p-toluenesulfonic acid.

6. The process of claim 3 whereby the process for preparation of Lapatinib ditosylate is a one-pot process in which no intermediates are isolated.

7. The process of claim 1 wherein the treating of the compound of Formula II with 2-methanesulphonylethylamine or a salt thereof occurs in the presence of a base.

8. The process of claim 7 wherein the base is N,N-diisopropylethylamine.

9. The process of claim 1 wherein the hydrogenation catalyst is selected from the group consisting of palladium on carbon, platinum on carbon and Raney nickel.

10. The process of claim 1 wherein the hydrogenation catalyst is palladium on carbon.

11. The process of claim 1 wherein the hydrogenation catalyst is 5% palladium on carbon.

12. The process of claim 1 wherein the treating of the compound of Formula II with 2-methanesulphonylethylamine or a salt thereof occurs in the presence of a solvent selected from the group consisting of alcohols and halogenated hydrocarbons.

13. The process of claim 1 wherein the treating of the compound of Formula II with 2-methanesulphonylethylamine or a salt thereof occurs in the presence of a solvent selected from the group consisting of methanol, dichloromethane and mixtures thereof.

14. A process for the preparation of Lapatinib or a ditosylate salt thereof comprising:
 i) treating, in the presence of a base and in the presence of a solvent selected from the group consisting of methanol, dichloromethane and mixtures thereof, a compound of Formula II:

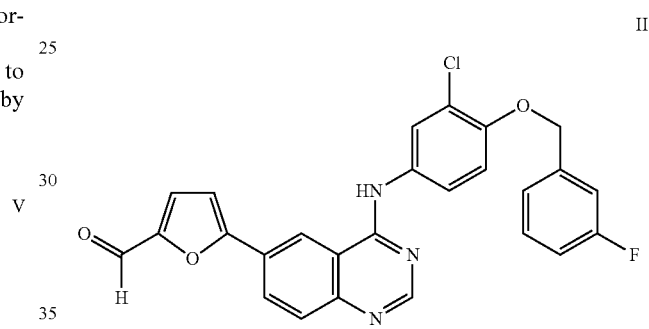

with 2-methanesulphonylethylamine or a salt thereof, thereby forming a product;
 ii) reducing the product in the presence of a suitable hydrogenation catalyst, which hydrogenation catalyst is selected from the group consisting of palladium on carbon, platinum on carbon and Raney nickel, thereby forming Lapatinib free base of Formula IV:

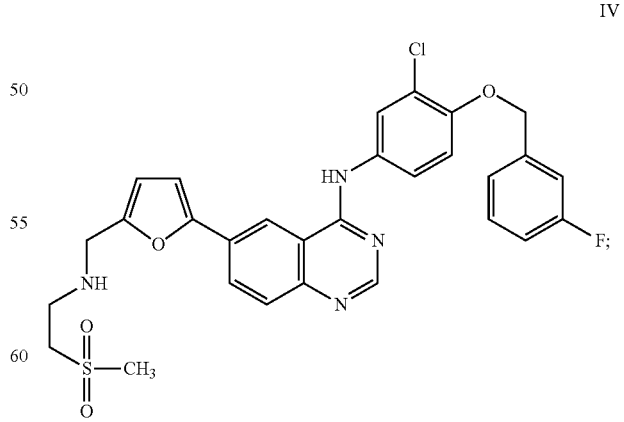

and
 converting the compound of Formula IV to Lapatinib ditosylate of Formula I:

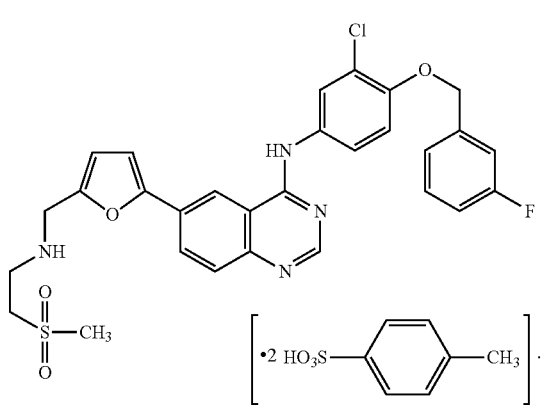

I

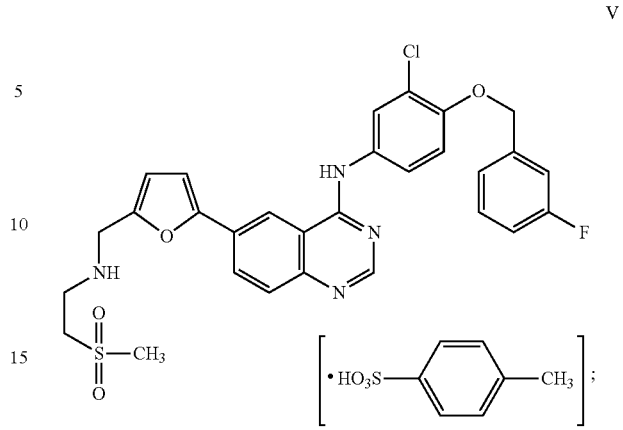

V

15. The process of claim 14 wherein the compound of Formula IV is not isolated before converting the compound of Formula IV to the Lapatinib ditosylate of Formula I.

16. The process of claim 15 wherein the base is N,N-diisopropylethylamine.

17. The process of claim 15 wherein the converting of the compound of Formula IV to the Lapatinib ditosylate of Formula I comprises:

i) treating the compound of Formula IV with about 0.8 to about 1.2 equivalents of p-toluenesulfonic acid, thereby forming monotosylate of Formula V:

and ii) treating the compound of Formula V with about 0.8 to about 1.2 equivalents of p-toluenesulfonic acid, thereby forming the Lapatinib ditosylate of Formula I.

18. The process of claim 15 wherein the conversion of a compound of Formula IV to Lapatinib ditosylate of Formula I comprises treatment of a compound of Formula IV with about 1.8 to about 2.2 equivalents of p-toluenesulfonic acid.

19. The process of claim 15 whereby the process for preparation of Lapatinib ditosylate is a one-pot process in which no intermediates are isolated.

* * * * *